US007532923B1

(12) United States Patent
Hayes-Gill et al.

(10) Patent No.: US 7,532,923 B1
(45) Date of Patent: May 12, 2009

(54) APPARATUS AND METHOD FOR DETECTING A FETAL HEART RATE

(75) Inventors: Barrie Hayes-Gill, Nottingham (GB); David James, Nottinghamshire (GB); John Crowe, Nottingham (GB); Jean-Francois Pieri, Cannes (FR)

(73) Assignee: Monica Healthcare Limited, Nottingham (GB)

( * ) Notice: Subject to any disclaimer, the term of this patent is extended or adjusted under 35 U.S.C. 154(b) by 639 days.

(21) Appl. No.: 10/089,997

(22) PCT Filed: Oct. 6, 2000

(86) PCT No.: PCT/GB00/03843

§ 371 (c)(1),
(2), (4) Date: Sep. 23, 2002

(87) PCT Pub. No.: WO01/26545

PCT Pub. Date: Apr. 19, 2001

(30) Foreign Application Priority Data

Oct. 8, 1999 (GB) .................................. 9923955.0

(51) Int. Cl.
*A61B 5/0444* (2006.01)
(52) U.S. Cl. ....................................................... 600/511
(58) Field of Classification Search .................. 600/511
See application file for complete search history.

(56) References Cited

U.S. PATENT DOCUMENTS

| 4,781,200 | A | * | 11/1988 | Baker ........................ 600/483 |
| 5,372,139 | A | * | 12/1994 | Holls et al. ................. 600/511 |
| 5,666,959 | A | | 9/1997 | Deans et al. |
| 5,807,271 | A | * | 9/1998 | Tayebi et al. ............... 600/511 |
| 6,115,624 | A | * | 9/2000 | Lewis et al. ................. 600/376 |
| 6,751,498 | B1 | * | 6/2004 | Greenberg et al. .......... 600/511 |

FOREIGN PATENT DOCUMENTS

FR            2 566 652           1/1986

OTHER PUBLICATIONS

"Lead systems for the abdominal fetal electrocardiogram," A van Oosterom, Clin. Phys. Physiol. Meas., 1989, vol. 10, Suppl. B, 21-26.*
Richter M., Schreiber T., Kaplan D.T., 'Fetal ECG extraction with nonlinear state-space projections', IEEE Trans. Biomed. Eng., vol. 45, No. 1, pp. 133-137, Jan. 1998.*

* cited by examiner

*Primary Examiner*—Carl H Layno
*Assistant Examiner*—Eric D Bertram (57) ABSTRACT

The present invention relates to apparatus for detecting the heart rate of a fetus. The apparatus includes at least two detectors for detecting heart beats of the fetus, each detector comprising at least two electrodes for detecting ECG signals. A processor, which is coupled to the detectors, is used to process the ECG signals received from each detector and determine the heart rate of the fetus.

6 Claims, 11 Drawing Sheets

APPARATUS AND METHOD FOR DETECTING A FETAL HEART RATE

The present invention relates to apparatus and a method for detecting the heart rate of a fetus.

It is useful to be able to detect the heart beat of fetuses as this can provide information regarding the health of the fetus during the progress of pregnancy. Currently there are four main methods for detecting fetal heart rates during pregnancy and these involve the use of Doppler ultrasound, a SQUID magnetometer, phonocardiography, and abdominal fetal electrocardiography.

The Doppler ultrasound technique consists of directing a 2 MHz (or other similar frequency) crystal transducer at the fetus on the mother's abdomen. The signal reflected from the fetus is shifted by a small frequency (known as the Doppler shift) which is due to the pulsation of the fetal heart, hence (after suitable processing) producing a fetal heart rate (fHR) trace. Portable Doppler systems exist but as with all single channel Doppler systems the transducer has to be periodically re-positioned to point at the fetus and this requires the intervention of clinically trained staff. Such systems are therefore limited to use in a hospital environment.

A multi-channel Doppler ultrasound unit has also been described in the document entitled "Fetal heart rate recorder for long-duration use in active full-term pregnant women", by Shono et al from Obstetrics and Gynecology, 1994 83, 2, page 301, which aims to be ambulatory. This consists of six Doppler transducers positioned on the abdomen with each being optimally positioned for the various stances of the mother during her day. However, due to the nature of the ultrasound signal being directed at the fetus then long term recordings of fHR using ultrasound may be considered as invasive. Although this invasive nature has not been clinically substantiated, the use of Doppler ultrasound is still limited to short time periods. Finally, the Doppler ultrasound technique only provides an averaged fHR and gives no information about: the beat-to-beat variability; nor about morphological information such as the one contained in the shape of the Fetal electrocardiogram (fECG) complex.

A SQUID magnetometer has been described in "Application of SQUID magnetometer in fetal electrocardiography" Applied Superconductivity, H Rogalla ed Inst, Physics Conf. Series, IOP, 1997, pp 21-26 by Rijpma et al. This describes a SQUID magnetometer that can record the magnetic field associated with the electric field generated by the fetal electrocardiogram (fECG). A transducer is placed on the mother's abdomen above the fetus and the corresponding fetal magnetic field can be detected using a sensitive SQUID magnetometer. However, the system requires complex circuitry and the SQUID transducer must be cooled to liquid helium temperatures, thus resulting in these systems being both expensive and large. Although long term recordings can be made they are nevertheless carried out in an environment, which due to the nature of the surrounding equipment, is neither comfortable nor easily accessible to a wider community.

Phonocardiography has been in existence for over 80 years and has mainly been applied to adults. The technique consists of using a microphone which can detect the audible sound of the blood flowing through the heart. Such a technique can be applied to the fetal heart during pregnancy but is highly susceptible to extraneous audible noises.

It is also possible to record an fECG by the insertion of a fine needle through the mother's abdomen and into the womb. This technique will give not only a reliable fHR but will also produce a reliable fECG complex. However, the technique is highly invasive and in some cases extremely risky, and accordingly can only be performed by a highly skilled medical team.

Another abdominal technique has been implemented by Visser et al and is described in "Diurnal and other cyclic variations in human fetal heart rate near term", Am. J. Obst. & Gynec., 142, 5, page 535. This system uses a single channel sub-cutaneous needle electrode to record long term fHR diurnal variations. Although not as invasive the technique does require some penetration of the skin and its avoidance is preferred.

The recording of fECG from the mother's abdomen has also been carried out using passive surface skin electrodes via a single analogue channel ECG machine. This is described in "Method and apparatus for indicating repetition intervals of a specified component of a composite electrical signal, particularly useful for displaying fetal R waves" U.S. Pat. No. 4,945,917 by Akselrod et al. The technique uses two electrodes which are placed approximately 10 cm to 20 cm either side of the umbilicus. The apparatus consists of an analogue front end having amplification and filtering. The output of this is fed into a bed-side computer for subsequent digitization and processing. As a result of the system requiring separate processing apparatus to process the obtained data as it is generated, the unit is not portable. The system is therefore only used for short time intervals, typically in the region of 20 minutes. Also, the system only uses a single channel and this means that for a large proportion of the time during which measurements are made, the fetal heart rate cannot be detected.

Multichannel abdominal fECG units have been presented in the literature in "The potential distribution generated by the fetal heart at the maternal abdomen", J. Perinat. Med. 14, page 435 by Oostendorp et al 1986. These system are used for vector cardiography (VCG) and for obtaining the shape of a single fECG complex. Measurements of this form are made in order to determine the shape of the electrocardiogram so as to determine fetal cardiac health. As a result, although the shape of individual heart beats are measured, the duration between these beats, and hence the fetal heart rate, is never determined.

In any event, in order to make the required measurements the system (which will require a large recording bandwidth) must therefore use a large number of recording channels, typically 32. As a result of this, the system utilizes large bedside units which are permanently positioned in a hospital. Not only does this therefore require that the mother spend a period of time in hospital for the monitoring to take place, but this also means that the equipment is not used for long-term fetal heart beat detection. In fact, measurement is typically made over a 45 second time interval. Finally, the electrodes are positioned indiscriminately on the abdomen without reference to fetal position.

Figure 1A:
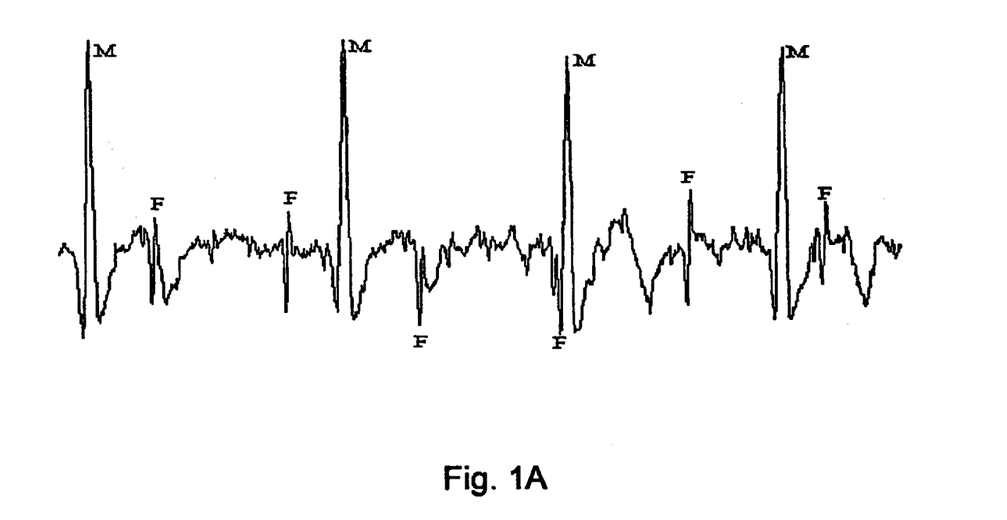
FIG. 1A shows a "good" output from a single channel detector.
Figure 1B:
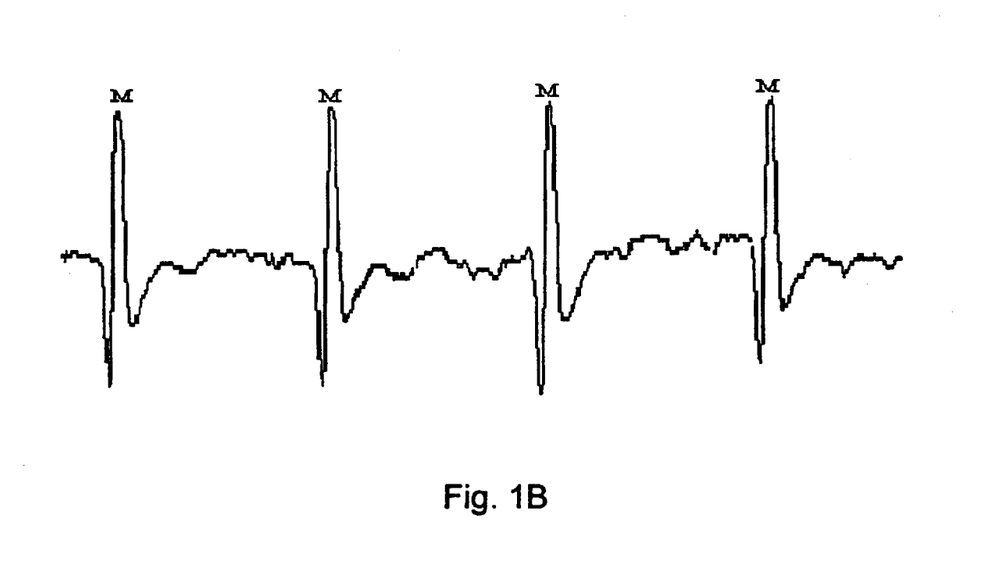
FIG. 1B shows a "poor" output from a single channel detector.

Typical results obtained from a single channel abdominal fetal ECG machine are shown in FIGS. 1A and 1B. FIG. 1A shows the data obtained from a "good" signal which shows definite fetal ECG's (F) along with the large maternal ECG's (M). However, "good" data is infrequently obtained and typically in 60% of cases the data is "bad" meaning that the fetal ECG (fECG) is undetectable. An example of such "bad" data, in which only the maternal ECG signal can be seen, is shown in FIG. 1B.

In a trial using this technique 300 recordings were made and the results of these were grouped into 'definite' fECG observation and 'not definite'. 38% of recordings were classed as 'definite'. Hence out of 10 mothers visiting the hospital the technique, in this form, will only be successful on typically 4 pregnancies—a figure which makes the technique unacceptable for routine spot checks of abdominal fECG.

During these recordings a note of fetal position for each recording was made by palpating the mothers abdomen. This was simply because the mother's abdomen during pregnancy can be considered as a sphere of diameter typically 50 cm and the fetus (sometimes with a fetal heart as small as 2 cm at early periods of gestation) could reside anywhere inside this sphere. Hence the use of a single pair of electrodes in the center of the abdomen only provides a compromise. The largest fECG would occur where conduction through the abdomen and other tissues is at its highest.

Analysis of the results shows that the largest fECG occurs at the shortest path from the fetal heart. For example, it was found, from the above 300 recordings, that when the fetus was engaged at the front-right of the abdomen the percentage success rate of 'definite' increased to 46% whilst those on the front-left had a percentage of only 32%. A possible explanation for this is that when the fetus is on the front-right and the two electrodes in the center of the abdomen, the fetal heart is close to these centrally positioned electrodes hence a larger fECG complex is detected. However, with the fetus on the front-left, the fetal spine masks the fetal heart from these electrodes hence attenuating the signal. Further, when the fetus was Another example of an acoustic fetal monitor is described in U.S. Pat. No. 4,781,200.

In accordance with a first aspect of the present invention, we provide apparatus for detecting the heart rate of a fetus, the apparatus comprising:

a detector for detecting heart beats of the fetus, the detector comprising at least two electrodes for detecting ECG signals, the detector being positioned on the abdomen of the mother in use; and, a processor coupled to the detectors, the processor being adapted to process the ECG signals received from each detector and determine the heart rate of the fetus, characterized in that the processor is further adapted to determine the heart rate of the mother by:
   a. detecting heart beats of the mother by determining when the ECG signals reach a maximum; and,
   b. determining the heart rate by determining the time interval between adjacent heart beats.

Accordingly, the present invention provides apparatus which is capable of detecting ECG signals produced by the fetal heart, and hence determine the heart rate of the fetus. In the preferred approach, at least two detectors detect the heart beats allowing two separate channels to be defined for carrying the ECG signals from a respective detector. Accordingly, should the fetus move such that one of the detectors is no longer able to detect the heart beat, then an ECG signal can still be obtained from the other detector via the respective channel.

Although the heart rate will not be detectable for the entirety of this hour, this still ensures that sufficient data is collected to allow the fetal heart rate to be accurately determined.

Furthermore, this allows a portable device to be produced which can be carried by the mother, thereby allowing the measurements to be made over a longer time interval than has previously been achieved.

Optionally, where two or more detectors are provided, a common electrode forms one of the electrodes of each detector. The use of a common electrode is particularly advantageous as it reduces the number of electrodes that must be positioned on the mother's abdomen. It also leads to several advantages regarding the signal processing. However, alternatively each detector may comprise two respective electrodes that are not common to any other detectors.

The electrodes are typically passive conductive cutaneous electrodes which, in use, electrically detect signals representing the electrical activity in the region of the mother's abdomen.

Typically the apparatus further comprises a signal processor for amplifying and filtering the signals detected by the detectors. This helps remove noise which is detected by the detectors, thereby improving the quality of the fetal heart beat signal. However, if the signal is strong enough, amplification or filtering may not be required.

Typically, the processor generates virtual ECG signals as a weighted sum of the ECG signals detected by the detectors, the virtual ECG signals representing the ECG signals that would have been obtained from a virtual detector positioned at a virtual location on the abdomen of the mother. By using multiple detectors and processing the signals obtained from the detectors, it is possible to derive ECG signals that would have been generated by a detector positioned at an alternative location on the mother's abdomen. This advantageously allows an ECG signal to be generated for an optimum detector location even if this detector location was not actually used. However, the processor may alternatively simply aggregate the ECG signals obtained from the detectors or may simply obtain the fetal heart rate results from any respective detector.

Typically each virtual ECG signal is generated dynamically so as to represent the ECG signals that would be received from a detector dynamically located on the mother's abdomen. This allows the optimum detector position to move as the fetus moves within the womb, thereby ensuring that an optimum signal is obtained at all times.

Typically the apparatus further comprises an output for displaying an ECG trace of the heart beat of the fetus (and the mother) in accordance with the detected ECG signals. However, any suitable form of output of the heart beat may be produced.

Typically the processor is adapted to determine the heart rate of the fetus (and the mother) from the ECG signals by carrying out the steps of:
   a. suppressing portions of signal representative of the heart beat of the mother;
   b. detecting heart beats of the fetus by determining when the remaining signal reaches a maximum; and,
   c. determining the heart rate by determining the time interval between adjacent heart beats.

Accordingly, by removing the portions of the signals which are representative of the mother's heart beat, this should only leave the fetal heart beat and any detected noise. The fetal heart beat can be detected by determining locations where the signal reaches a maximum (or minimum) amplitude. However, any suitable method of detecting the fetal heart beat within a signal, such as estimating the point at which the heart beat should appear, or comparing the signal to a predetermined threshold could be used.

Typically the processor is further adapted to perform the steps (a), (b), and (c) on the ECG signals detected by each detector and then aggregate the obtained heart rate over a predetermined time period of not less than one hour. However, any suitable method of processing the ECG signals may be used.

Typically the apparatus is portable such that it can be carried around by the mother without placing any undue burden on the mother. This allows the apparatus to be used over a long time periods without disturbing the mothers normal routine.

It will be realized that although at least one detector is specified, the present invention may be utilized with any suitable number of detectors which does not cause discomfort to the mother.

In accordance with a second aspect of the invention, we provide a method of determining the heart rate of the fetus by using apparatus having a detector for detecting ECG signals representative of the heart beat of the fetus, the method comprising:

a. determining the position of the fetus within the womb;
 b. placing the detector on the abdomen of the mother, the detector being positioned in accordance with the position of the fetus;
 c. monitoring the ECG signals obtained from the detector for a predetermined length of time, the predetermined length of time being greater than one hour; and,
 d. processing the ECG signals obtained from the detector to determine the heart rate of the fetus.

Accordingly, the present invention also relates to a method of operating apparatus having one or more detectors to thereby obtain the best fetal heart rate detection. This is achieved by positioning the or each detector on the abdomen of the mother in accordance with the position of the fetus within the womb, thereby maximizing the chance of obtaining a signal from any one detector. Additionally by measuring the signals over a longer duration, this allows a larger amount of data to be detected which can be analyzed to obtain information regarding the heart beat of the fetus. This is particularly advantageous as the heart beat of the fetus is generally only detectable for about 40% of the time for any given detector. This is due to noise and movement of the fetus within the womb. Furthermore, by having multiple detectors, should the baby move so that the fetal heart beat can no longer be detected by one of the detectors, then there is a high probability that it will then be detected by another detector.

Typically, the signals obtained from each channel are monitored for a predetermined length of time. This is preferably greater than 12 hours. It will be realized however that longer durations may also be used.

Typically the method of determining the position of the fetus within the womb comprises palpating the mother's abdomen. Thus, this uses a simple non-invasive procedure for determining the position of the fetus. Alternatively however ultrasound, or other suitable techniques, could be used to locate the fetus.

The method of processing the ECG signals typically comprises the steps of:

a. suppressing portions of the ECG signals representative of the heart beat of the mother;
 b. detecting heart beats of the fetus by determining when the remaining ECG signals reach a maximum; and,
 c. determining the heart rate by determining the amount of time between adjacent heart beats.

Thus, this advantageously provides a method of processing the signals to determine the heart rate. However, any suitable method, such as comparing the ECG signals to a threshold, can be used.

Typically, where there is more than one detector, the method of processing the signals further comprises repeating steps (a), (b), and (c) on the ECG signals detected by each detector and then aggregating the obtained heart rate over a predetermined time period of not less than one hour. By aggregating the ECG signals obtained from different detectors, this means that the heart rate can be determined at any time during which at least one of the detectors is detecting fetal ECG signals. Alternatively however the signals can be processed so as to generate virtual ECG signals and this is achieved by determining a weighted sum of the ECG signals obtained from each of the respective detectors.

Typically the step of removing portions of signals representative of the heart beat of the mother comprises locating maternal ECG signals representing the heart beat of the mother, and subtracting the maternal ECG signals from the ECG signals obtained from each detector. This therefore advantageously removes the portion of the ECG signal which is due to the ECG signal generated by the mother's heart beat. However alternatively, the portion of the ECG signals which are due to the mother's heart beat can be ignored. In this case, any ECG signal obtained during the mother's heart beat is simply removed from the ECG signals which are then analyzed to determine the fetal heart rate.

It will be realized from this that the invention can advantageously be used to detect the heart beat of the mother, although these could be detected by separate apparatus. This is achieved by:

a. detecting heart beats of the mother by determining when the ECG signals reach a maximum; and,
 b. determining the heart rate by determining the time interval between adjacent heart beats.

However, it is not essential that the heart rate of the mother is detected.

Preferably the method of determining the heart rate by determining the time interval between adjacent heart beats comprises:

a. determining the standard deviation of each time interval for the heart beats detected during the predetermined time; and,
 b. selecting the time intervals having a standard deviation lower than a predetermined value.

However, the selection of erroneous time intervals could simply be determined by comparing heart rate indicated by the time interval to a threshold to identify time intervals indicating heart rates that are physically impossible. Alternatively, the fetal heart rate could be determined directly from the raw ECG signals, without analysis of the time intervals and the like.

The predetermined value is preferably approximately 7 ms for four consecutive time intervals, although any suitable value could be chosen by the user.

Typically the method further comprises:

a. designating time intervals not selected to be erroneous time intervals; and,
 b. modifying the erroneous time intervals in accordance with the selected time intervals.

Alternatively however, the erroneous time intervals could simply be ignored, although this results in a reduced amount of data from which the end heart rate is calculated.

Typically the method of modifying the time intervals comprises:

a. comparing the erroneous time interval to the selected time intervals;
 b. determining the number of errors within the erroneous time interval; and,
 c. dividing the erroneous time interval into a number of corrected time intervals by adding a number of heart beats corresponding to the number of errors to thereby subdivide the erroneous time interval.

However, any suitable method may be used.

The method generally further comprises averaging the time intervals and the corrected time intervals to determine a heart rate.

Typically the apparatus further comprises a signal processor for amplifying and filtering the ECG signals detected by the detector. Although this may not be required if the signals are of sufficient strength that the amplification is not required.

By accepting that the signal can only be detected in any patient for approximately 40% of the time using a single detector, we have developed a system that is portable, can be used for 24 hours or longer, has more than one recording channel and is extremely low noise. By initially deducing the baby position a small array of electrodes can be placed around the fetus on the mother's abdomen—thus increasing the detection rate. By recording over 24 hours using our improved technique will typically result in at least 10 hours of data. This long term, non-invasive collection of fHR data allowing mothers freedom to function in their normal environment has never been achieved before.

Examples of the present invention will now be described with reference to the accompanying drawings, in which:—

Figure 2:
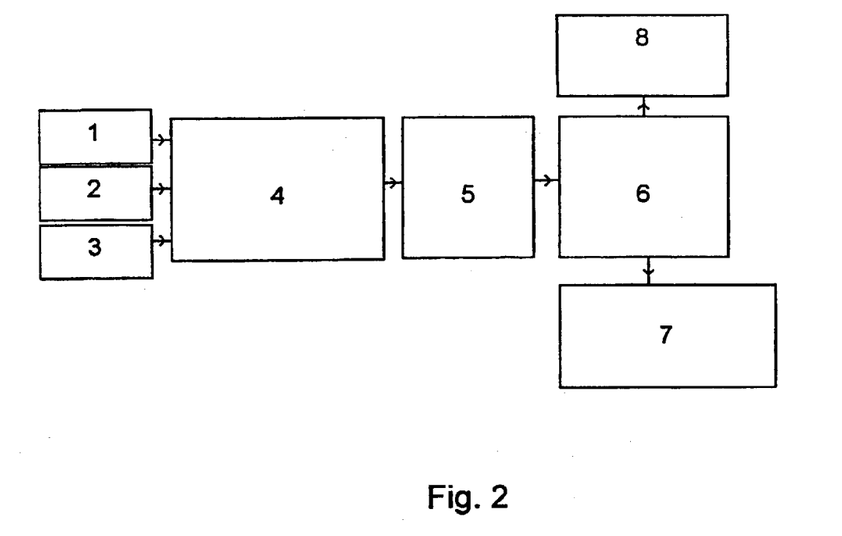
FIG. 2 is a block diagram of apparatus for detecting the heart beat in accordance with the present invention.

FIG. 2 is a block diagram showing apparatus for detecting the heart beat of a fetus. The apparatus comprises three detectors 1,2,3 which are coupled to an amplification and filter stage 4. The output of the amplification and filter stage 4 is coupled to an analogue-to-digital converter 5, which is in turn connected to a processor 6. The processor 6 is coupled to a memory 7 and a display 8.

Figure 3:
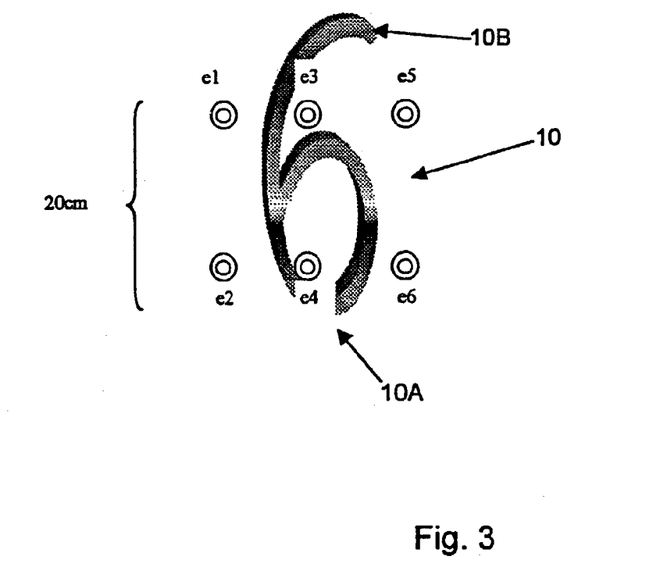
FIG. 3 is a first example of the detector arrangement of the apparatus shown in FIG. 2.

The system operates as follows. Each detector 1,2,3 consists of two passive cutaneous conductive electrodes positioned on the abdomen of the mother so as to detect ECG signals generated in the region of the mother's abdomen. An example of a suitable electrode arrangement is shown in FIG. 3. In this case, the electrodes e1,e2 correspond to detector 1, electrodes e3,e4 correspond to detector 2 and electrodes e5,e6 correspond to detector 3. Reference numeral 10 represents the fetus, with 10A representing the head and 10B the fetal back.

Electrical signals detected by the detectors 1,2,3 are fed into the amplification and filter stage 4 via a respective analogue channel. Each analogue channel has a very low noise (better than 75 nV (RMS) equivalent to an average of 17 nv/Hz$^{1/2}$).

Although this example is described with respect to three channels, one or more channels, coupled to respective detectors, could be used. Increasing the number of channels and detectors will increase the success of heart beat detection, however this will be at the expense of inconveniencing the mother by having several electrodes placed on her abdomen. In any event, further increases in the success of heart rate detection can be achieved by monitoring generated ECG signals for long time periods as will be explained in more detail below. This can be achieved by the use of the apparatus of the invention which is portable, allowing readings to be taken over extended time periods without inconveniencing the mother.

The signals output from each detector 1,2,3 are transferred to the amplification and filter stage 4 for amplification and subsequent filtering. This is typically achieved using two stages of amplification and filtering which are software programmable. The overall gain can be set typically from 1000 to 5000 and will typically have a bandwidth of approximately 4-80 Hz. However, in cases with low patient noise a bandwidth of 0.5-250 Hz can be set.

The amplified and filtered signals are passed onto the analogue-to-digital convertor 5 which operates to convert each of the signals into a digital signal which is then passed onto the processor 6. Accordingly, the processor unit receives three digital signals corresponding to a respective one of the detectors 1,2,3.

The processor handles memory storage, real time processing and display of the digitized signals. The data is stored in the memory 7, which is typically some form of large capacity flash semiconductor storage. This form of device is particularly advantageous as it may be located inside the instrument, is non-volatile and can be removed for subsequent downloading of data.

The processing of the data to extract the fetal heart rate can be implemented either "on-line" within the processor 6, or "off-line". In the on-line case, the result of the processing can simply be displayed on the display 8. Otherwise, the data is typically downloaded onto a PC for additional processing.

As mentioned in the introduction, whilst testing previous techniques, 300 recordings were made using a single channel detector. Using the results of these previous 300 recordings, knowledge determined from these was then applied in carrying out a test of the apparatus shown in FIG. 2. In this case, the electrode arrangement shown in FIG. 3 was utilized.

Figure 4A:
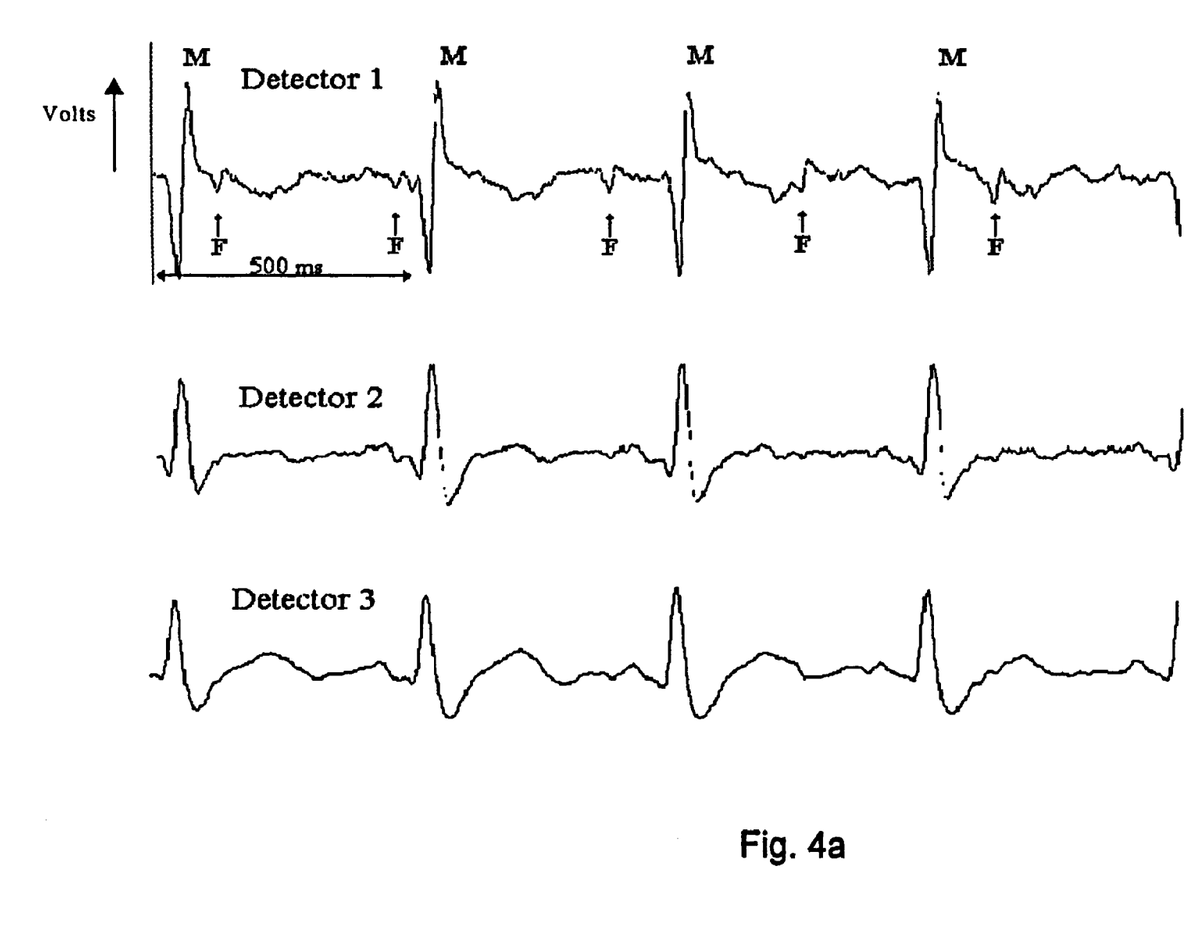
FIGS. 4A and 4B are examples of the output obtained from the detector arrangement of FIG. 3.
Figure 4B:
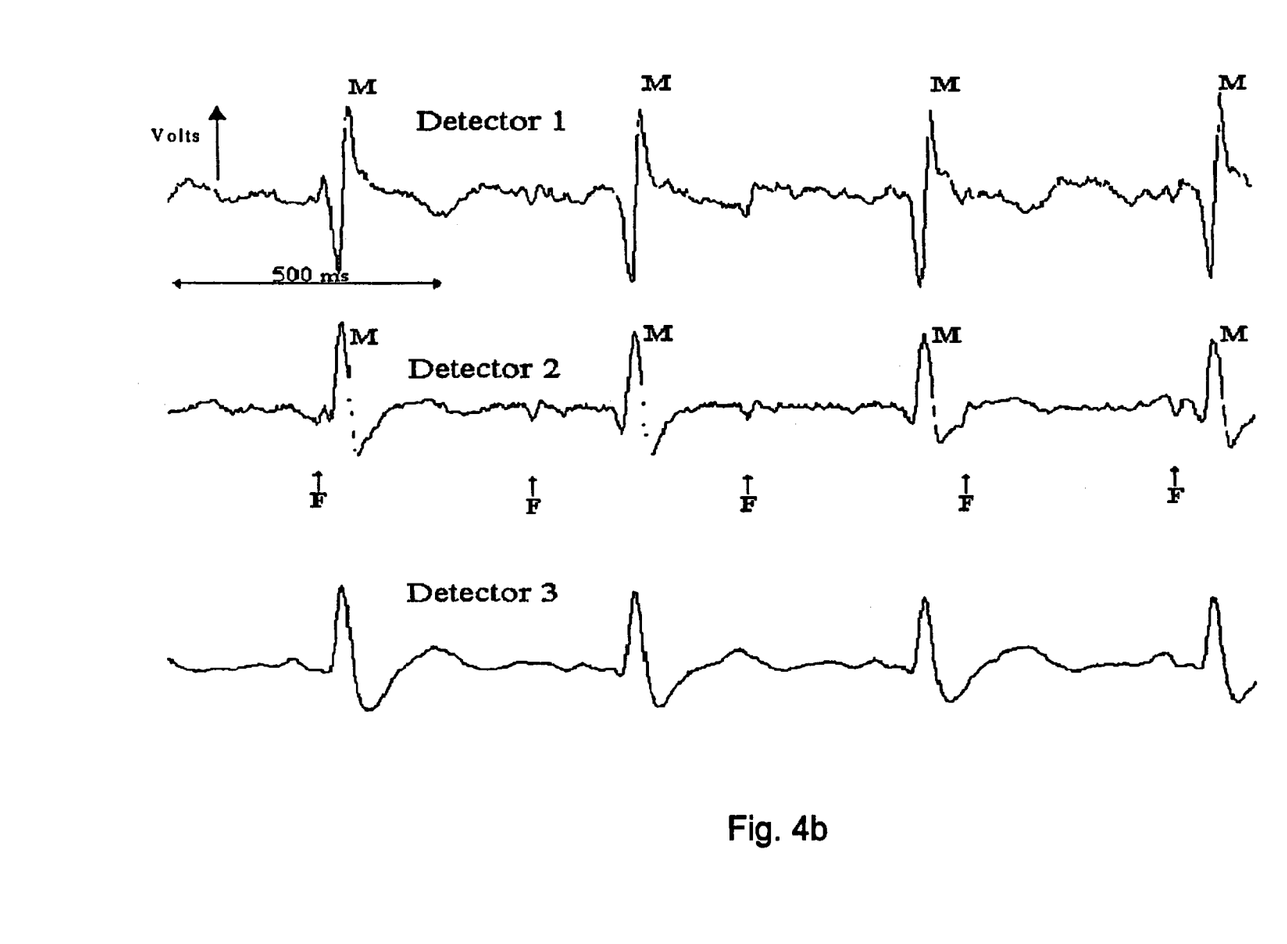

The results of one such test are shown in FIGS. 4A and 4B which show the amplitude of signals detected by the detectors 1,2,3 against time, with the output of each channel being shown on a similar scale graph. In this case, the test was carried out during a 10 minute period and this shows that during the early part of the 10 minute period, shown in FIG. 4A, the fetal heart beat is detectable using detector 1. However in a later part of the 10 minute period, which is shown in FIG. 4B, the fetus has moved and the fetal heart beat is now detected by detector 2.

Accordingly, knowledge of fetal position and the presence of an array of electrodes (i.e. more than one detector) leads to an increase in the percentage success of fetal heart beat detection. Thus using more than one detector 1,2,3 and positioning the detector electrodes around the periphery of the located fetus dramatically increases the success rate. It is important to note that the central point of this array of electrodes on two totally different patients could be separated by as much as 50 cm. Hence the knowledge of fetal position is important with regard to correct electrode positioning.

The electrode arrangement shown in FIG. 3 is a 3-channel system with differential inputs. In this case, 6 electrodes e1,e2,e3,e4,e5,e6 are positioned as shown, with an additional ground connection electrode (not shown) located on the back of the patient. The exact positioning of the electrodes will vary from case-to-case, although the electrodes of a given detector (e.g. the electrodes e3 and e4) are typically positioned such that e4 lies beneath the umbilicus but above the symphysis pubis and e3 at the fundus (this distance is typically 20 cm apart). This six electrode technique offers the attraction of 3 separate channels thus reducing any common muscle noise (i.e. electromyogram or EMG).

As the apparatus shown in FIG. 2 uses a minimum number of components, it can be incorporated into a small portable device which may measure 14 cm by 10 cm by 3 cm or smaller. In addition to this, the apparatus is implemented using semiconductor electronics and is therefore extremely light such that it can be easily carried by the mother. As a result, the apparatus is portable in the sense that it can be strapped to the mother and the electrodes attached without it being intrusive into the mother's everyday routine. This allows the mother to attach the apparatus for extended periods of time, such as 24 hours, allowing measurements to be made over longer time periods.

Figure 5:
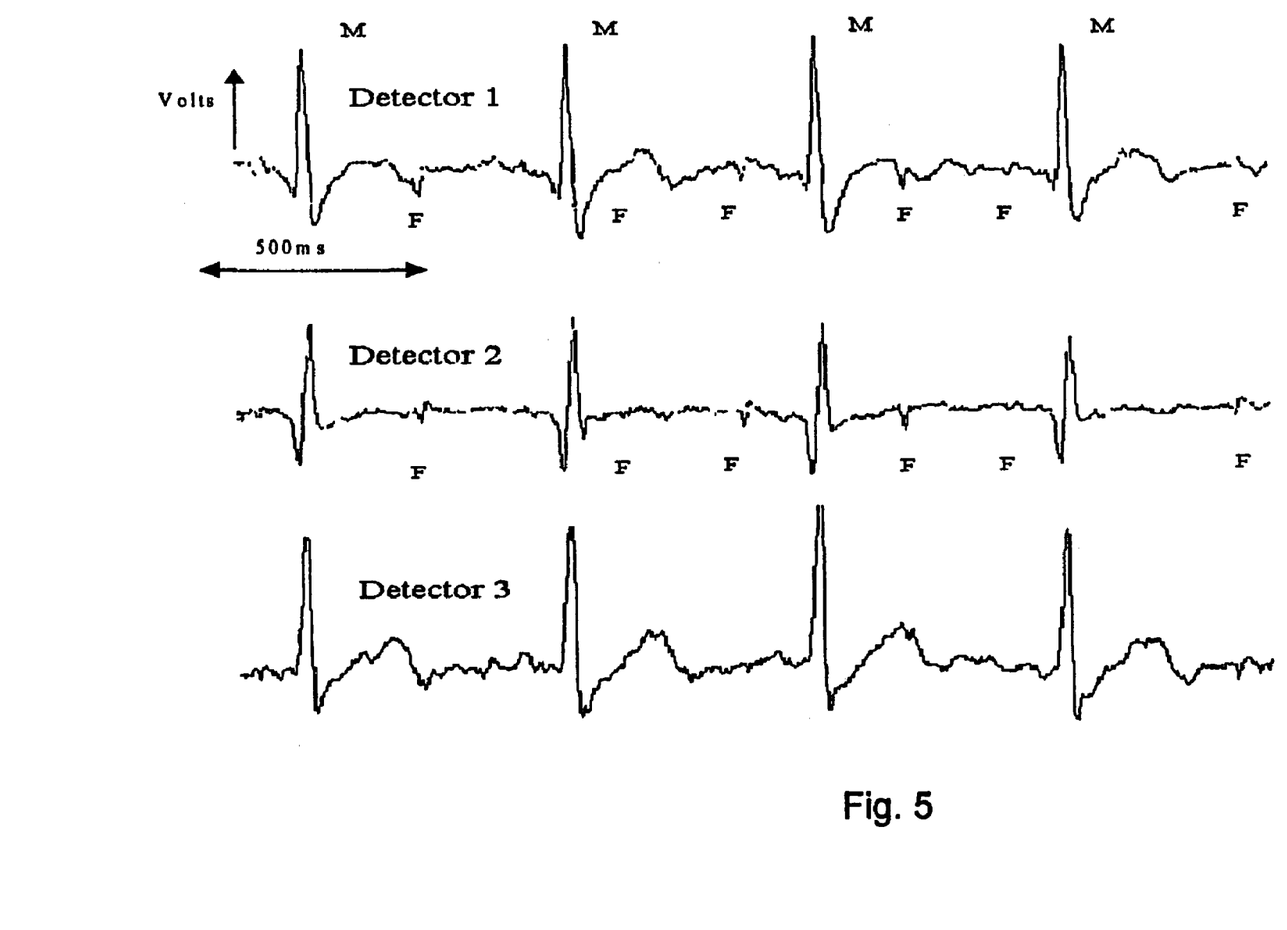
FIG. 5 is a second example of an output obtained from the electrode arrangement of FIG. 3.

A short extract from a 24 hour recording using three detectors, simultaneously, is shown in FIG. 5, which again shows the amplitude of the electrical signal detected against time. In this case, at the time of the extract, the fetal heart rate can be seen in the ECG signals obtained from both the detector 1 and the detector 2.

Once the raw data has been obtained, the processor 6 operates to extract the fetal heart rate (fHR) for each channel using techniques described in more detail below.

Figure 6:
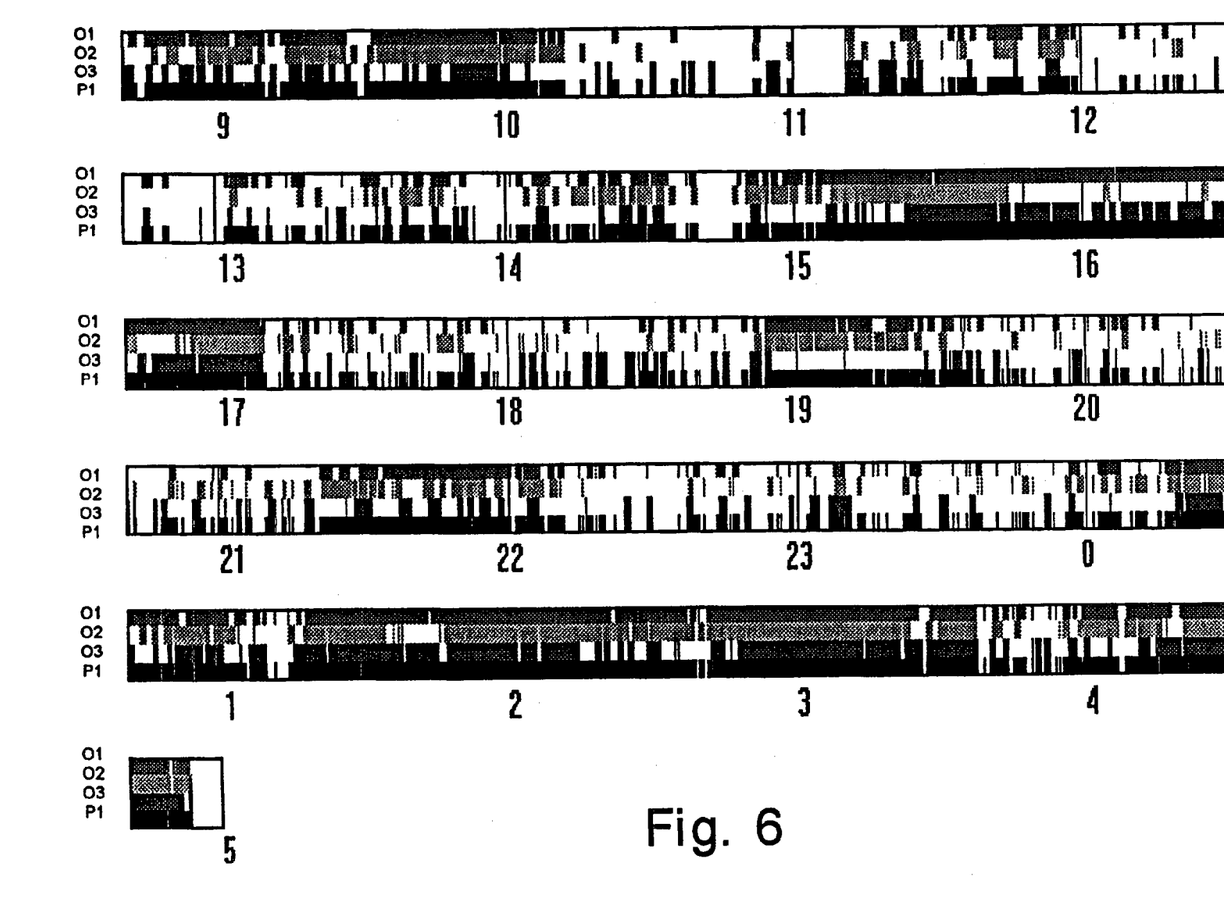
FIG. 6 is an example of fetal heart rate together with an aggregate fetal heart rate obtained from the detector arrangement of FIG. 3.

This results in the output traces shown in FIG. 6. This shows the time (in hours) during which heart beat detection occurred. Time periods when a heart beat could be detected are shown as a solid bar-graph with the output obtained from detectors 1,2,3 labeled O1,O2,O3 respectively. Times when no heart beat could be detected are indicated by blank portions B. The individual percentage success rates for times when a fetal heart beat could be detected in this case were:

| Channel | fHR extraction success rate |
|---------|------------------------------|
| 1 (O1)  | 36%                          |
| 2 (O2)  | 24%                          |
| 3 (O3)  | 19%                          |

However, the processor 6 is configured to determine an aggregate of these 3 channels which is shown in FIG. 6 as P1, here we obtain a percentage success of 67%. This increase occurs because when the fECG signal is not detected by one of the detectors 1,2,3, at least for some of the time it is detectable by one of the other detectors 1,2,3.

However, it is more acceptable for the mother if fewer electrodes are used. This can be achieved by using a single detector electrode common to all three detectors 1,2,3 with the common electrode being coupled to either an inverting or non-inverting input of the amplification and filter stage 4.

Figure 7A:
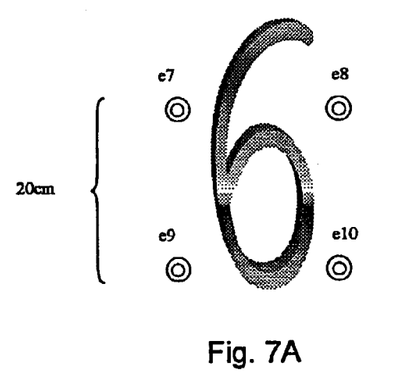
FIG. 7A shows a second example of an electrode arrangement used in the apparatus of FIG. 2.
Figure 7B:
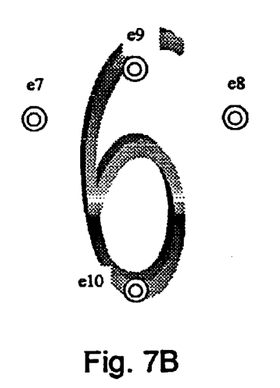
FIG. 7B shows a third example of an electrode arrangement used in the apparatus of FIG. 2.

In this case only four electrodes e7,e8,e9,e10 are required to form the three detectors 1,2,3 as shown for example in FIGS. 7A and 7B. Of the two arrangements the one shown in FIG. 7A is more suitable for fetuses at a later stage of gestation. Here the fetus is more stable and does not move around as much. The 'kite' shape shown in FIG. 7B is suitable for fetuses in the early stages of gestation where fetal position varies considerably.

In the case of FIGS. 7A and 7B each detector will measure ECG vectors with respect to the common electrode e10 thus allowing other mathematical combinations to be produced. These are known as virtual detector outputs, as the processed output represents the output that would have been obtained from a detector having respective electrodes positioned elsewhere on the mother's abdomen.

The virtual detector outputs are calculated using Kirchoff's voltage law which allows the processor 6 to mathematically combine the ECG signals obtained from each of the detectors 1,2,3. This can be achieved because the four electrode arrangements use a common electrode e10.

In this case, the virtual detector outputs are generated using a weighted sum of the amplitude signals obtained from each detector 1,2,3. This allows the virtual detector output to indicate an increased presence of fECG signals than is obtained with any one of the detectors 1,2,3 on its own. In other words, a more optimum virtual electrode position is simulated with the relative position of the electrodes depending on the weighting coefficients which are used when determining the weighted sum.

Figure 8:
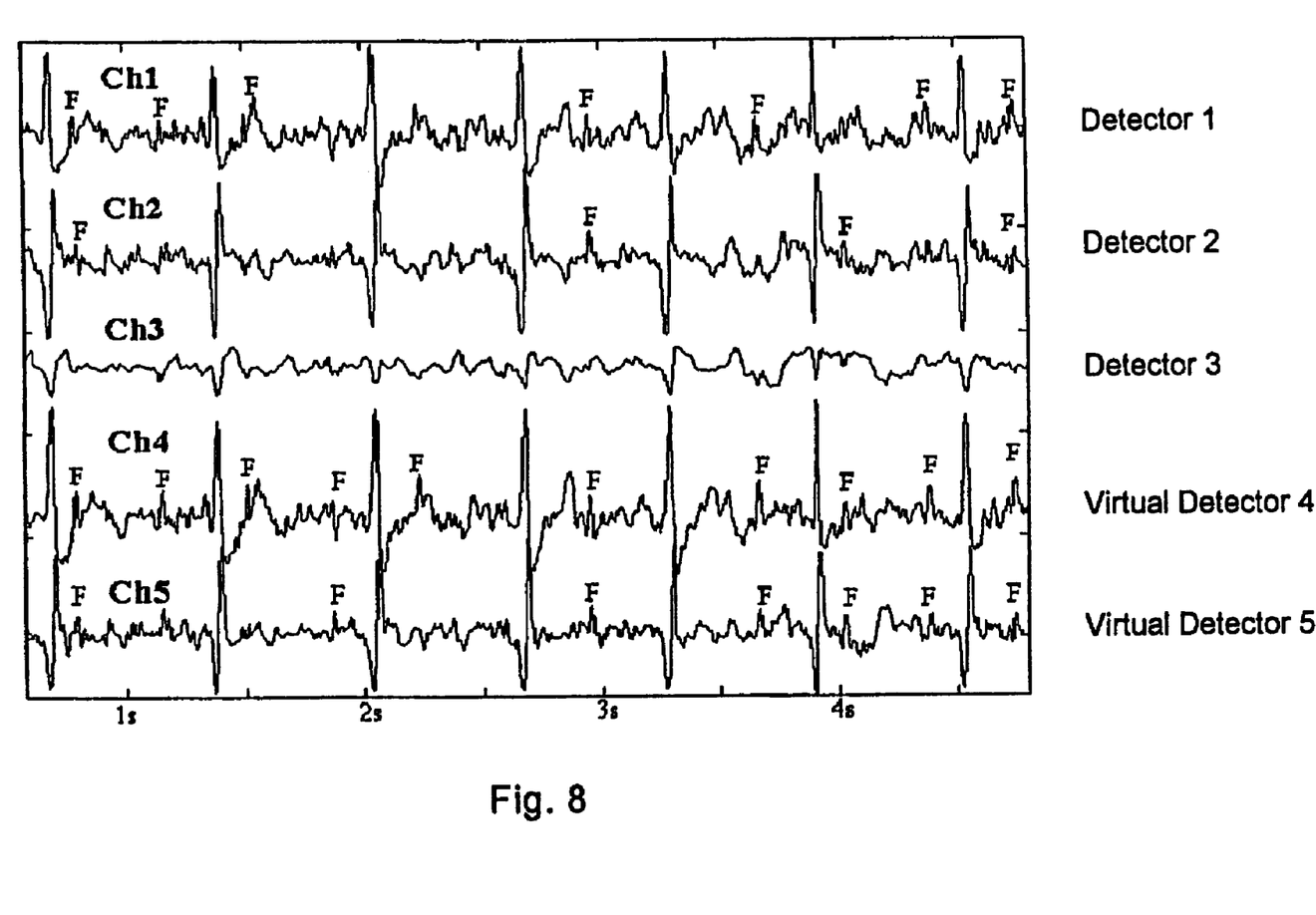
FIG. 8 shows an example of the output obtained from the electrode arrangement of FIG. 7A.

An example of this is shown in FIG. 8 which shows the amplitude of the ECG signals detected by the detectors against time. The signals detected by the detectors 1,2,3 are labeled detector 1, detector 2 and detector 3 respectively. Virtual detector 4 and virtual detector 5 represent the results of the calculation of the virtual detector output signals that would have been generated by two different virtual electrode positions. In this case, virtual detector 4 is determined by subtracting the output from detector 1 from the output from detector 2, whereas virtual detector 5 is determined by subtracting the output from detector 1 from the output detector 3. Again, the location of fetal heart beats is indicated by the label F.

Figure 9:
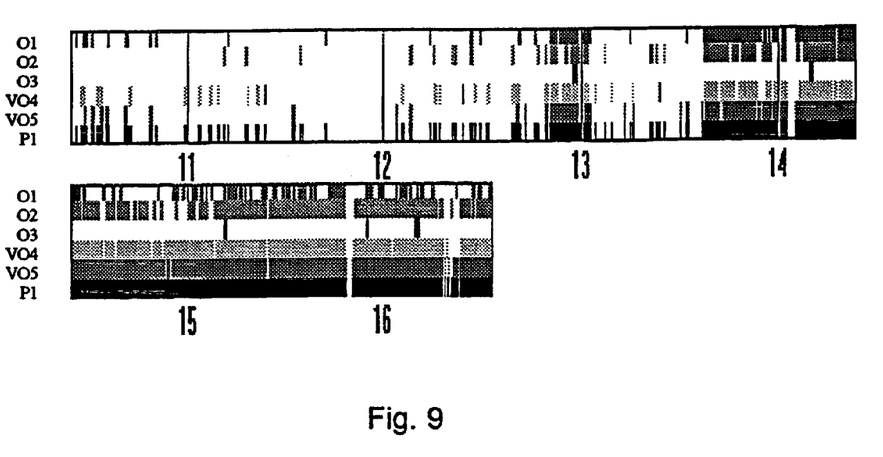
FIG. 9 shows an example of the heart rate obtained from the electrode arrangement of FIG. 7A.

The success for the detection of the heart rate for each channel is shown in FIG. 9, which is a bar-graph showing the time in hours during which heart rates were detected. Again, times during which heart rates were detected are represented by a solid bar. In this example the output obtained from the detectors 1,2,3 are labeled O1,O2,O3 respectively, and the output calculated for the virtual detectors 4,5 are labeled V04,V05. The percentage success for each channel and each virtual channel are tabulated below:

| Detector              | fHR extraction success rate |
|-----------------------|------------------------------|
| 1 (O1)                | 15%                          |
| 2 (O2)                | 31%                          |
| 3 (O3)                | 4%                           |
| Virtual detector (V04)| 34%                          |
| Virtual detector (V05)| 44%                          |

Again if we take an aggregate of channels 1, 2 and 3 we get an improvement to 35%. However, an aggregate of all five channels (including the virtual channels) gives an increased percentage of 48% as shown by the bar labelled P1 in FIG. 9. Hence, for this patient alone this results in an increase in the percentage from 4% (worst case) on a single channel system to 48% by the use of 3 channels and mathematical combinations to form these virtual channels.

It is also possible to calculate a dynamically changing optimum virtual detector output in real time and hence produce a single virtual detector output having the largest fECG complex possible. This is achieved by using a weighted sum of the signals output from all three detectors, with individual weighting coefficients, adjusted iteratively such that the fetal signal-to-noise ratio is maximized.

A secondary advantage of the presence of 3 detectors is the addition of redundancy to the system in the event of a failure on one detector caused by saturation. Saturation can occur when one electrode is depressed or leant upon.

This is a common problem in abdominal fECG monitoring. By having 3 detectors, this reduces the probability of this occurring.

The worry with traditional single channel abdominal fECG techniques has been that if employed for spot checks (i.e. a 20 minute ante-natal visit) only 4 out of every 10 mothers would present successful abdominal fECG traces.

Using the 3 channel system described above and then making use of the virtual channels still does not provide a certainty of detecting a fetal ECG. However, if this apparatus is used to record data over 24 hours then the probability of detecting a continuous 20 minute fHR trace which can be analyzed by the clinician is a near certainty.

Hence, assuming that the instrument and patient are noise free then in order to achieve this high percentage the procedure summarized below should be followed:—
  i. Find fetal location.
  ii. Use multi-channel recorder (three, but any number greater than two would preferably suffice).
  iii. Position electrodes in an array but use a common electrode so that virtual channels can be generated.
  iv. Record for 24 hours.
  v. Compute virtual channels either real time or off-line.
  vi. Extract fHR on all channels including virtual channels.
  vii. Calculate the total aggregate of all fHR channels including virtual channels.

In order for the processor 6 to extract the heart rate from the digitized output signals, one of the following techniques can be used.

Technique 1

Figure 10:
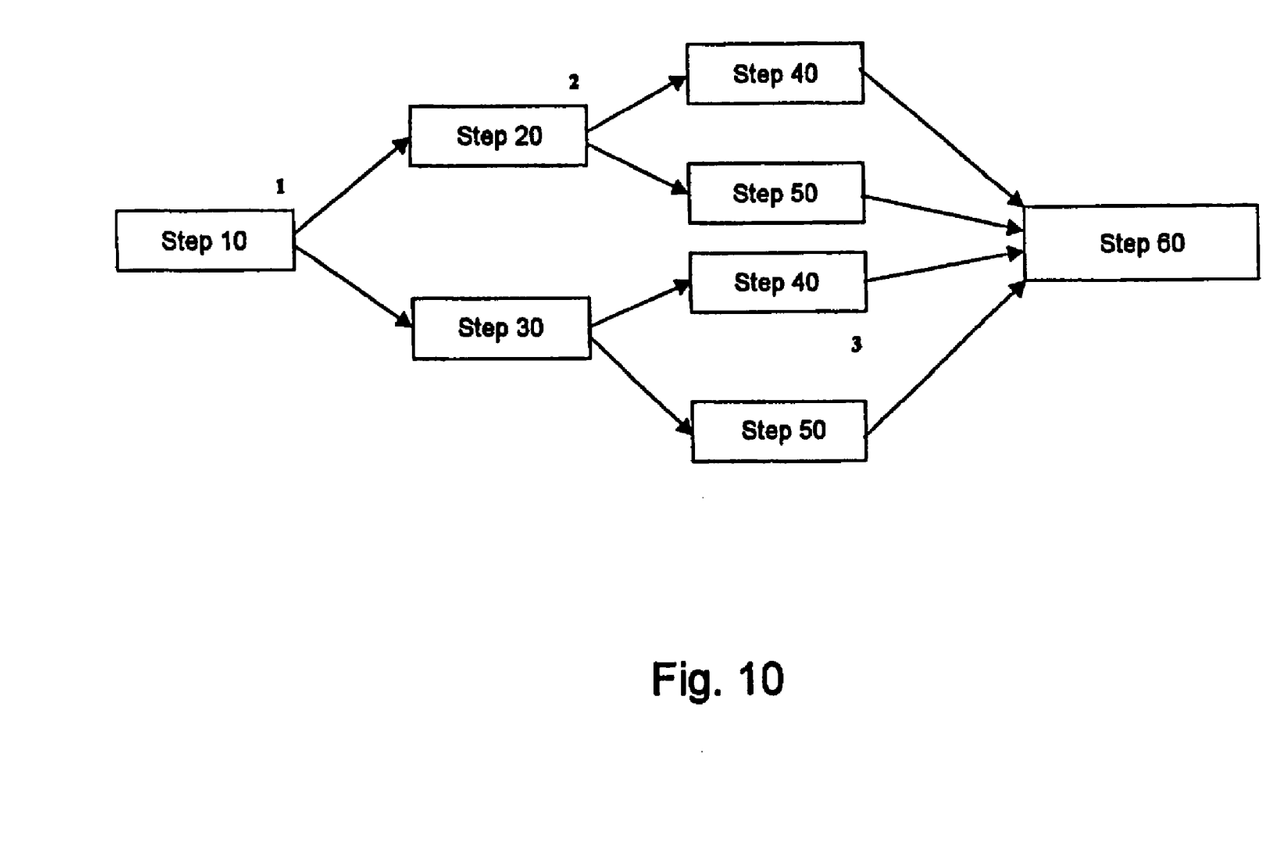
FIG. 10 shows an example of the method of processing the output obtained from the apparatus of FIG. 2.

The first technique is outlined in FIG. 10, which shows a block diagram of the steps involved in the first technique for extracting the fetal heart rate from the obtained ECG signals. This will be described with respect to FIGS. 11A to 11E which show the amplitude of an ECG signal against time, during the processing steps.

Figure 11A:
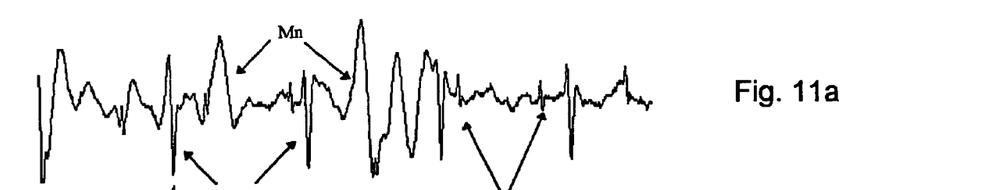
FIGS. 11A to 11E are graphs of the amplitude of an ECG signal against time for various processing stages; and, FIGS. 12A to 12D show the variations in fetal heart rate over time for various processing stages.

The raw ECG signals received from one of the detectors 1,2,3 are shown in FIG. 11A. The signals resulting from muscle noise are labeled Mn, the fetal heart beat is labeled F, and the mothers heart beat M. Coincident fetal and maternal heart beats are labeled M&F, whilst coincident fetal heart beats and muscle noise are labeled F&Mn.

The first stage, shown as step 10, is to correlate the obtained ECG signals with the ECG complex of the mother.

Figure 11B:
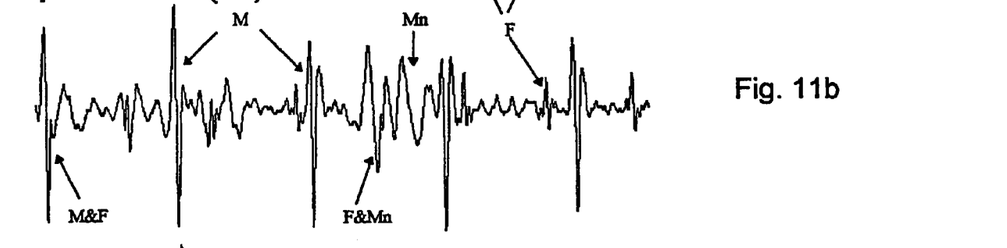
Figure 11C:
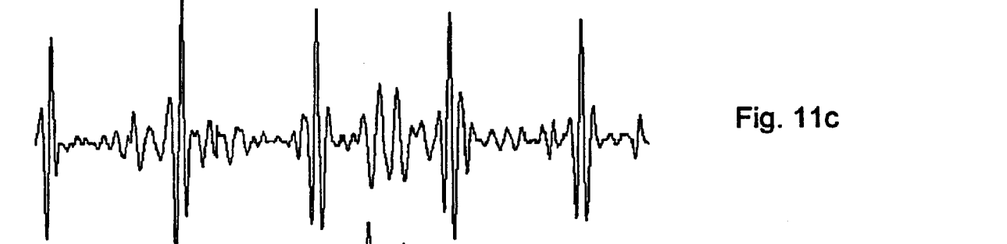

This is achieved by filtering the raw ECG signals first using a 10-80 Hz filter to reduce the amount of noise. The results of this filtering are shown in FIG. 11B.

Next, a maternal template is established using the average of 5 maternal complexes at initialization and then 32 complexes during the remaining time. This template is correlated (often called matched filtered) with the raw ECG to produce the trace shown in FIG. 11C. The maternal ECG's can then be located by detecting the maximum of this correlation.

Figures 11D, 11E:
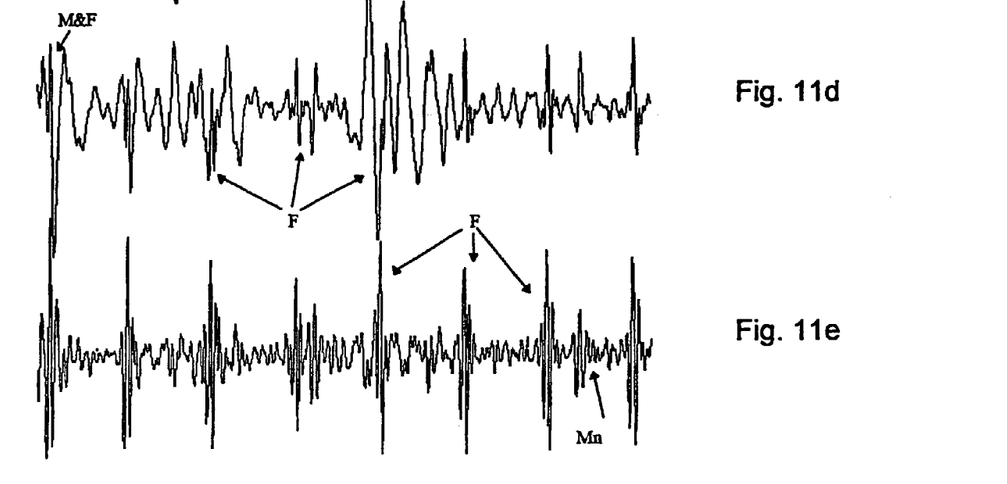

Two options are then available for removing the maternal ECG. Firstly, as shown at step 30, the maternal average ECG complex template can be subtracted from the ECG signal. The remaining ECG trace, which is shown in FIG. 11D, consists of fetal ECG and remnant noise.

Alternatively, as set out in step 20 in FIG. 10, the maternal ECG can be blanked out. This is usually used when subtraction of the maternal ECG leaves a remnant signal that is too often mistaken for a fetal ECG complex. The blanking technique (labeled in FIG. 10) can be used here. This involves locating the maternal as before (i.e. with correlation) and then simply drawing a straight line (or a simple interpolated function such as a spline) between the edges of the maternal ECG complex on the raw abdominal ECG trace. Although this can also remove fetal ECG complexes which are coincident with the maternal it can be regenerated during 'post-processing' which will be described in more detail below.

Once completed, the fetal heart beat must be detected and this can again be achieved using two different methods. The first method, shown as step 40 in FIG. 10, is to correlate the signal to detect this fetal ECG complex. The other method, step 50, involves band-pass filtering the signal using a 25-40 Hz filter or similar. Both techniques enhance the fetal ECG complex and hence improve the signal-to-noise ratio. However, the band-pass filtering technique usually results in a more stable output and an example of this is shown as FIG. 11E.

Finally the fetal heart beats are determined by identifying the maxima of the resulting ECG trace in step 60.

It should be noted that if a fetal heart beat is located during the maternal subtraction window then this fetal is tagged in the fHR data file as 'coincident'-referred to as "coincident flag". This is because it may in fact be an artefact caused by maternal subtraction and can be allowed for during post-processing.

Technique 2

The second technique involves a Non-Linear Filtering technique described by Thomas Schreiber. Details of this can be found for example in either of the following references:

Kantz D., Schreiber T., 'Nonlinear time series analysis', Cambridge Univ. Press, 1997.

Richter M., Schreiber T., Kaplan D. T., 'Fetal ECG extraction with nonlinear state-space projections', IEEE Trans. Biomed. Eng., Vol. 45, No. 1, pp 133-137, January 1998.

The outputs from this non-linear technique produce 'semi-clean' mECG and fECG traces. This data is then passed through a band-pass FIR filter. The bandwidth of the filter is 4 Hz to 40 Hz for the mECG and 25 Hz to 40 Hz for the fECG to remove any remnant noise not cleaned by the non-linear filtering. The maxima of the output of the filter are then located to obtain again the raw beat to beat heart rate files for maternal and fetal.

In both the above mentioned techniques, the fetal heart rate is measured by determining the time interval between adjacent heart beats and then using this to derive a heart rate. Once the data representing the heart rates has been obtained, it is then possible to carry out further post-processing of the raw maternal and fetal heart rate data to further improve the results of the heart rate determination.

The processing described in the above two techniques generates 'raw beat-to-beat heart rate values' for both maternal and fetal. Incorrect heart rate values can exist in both fetal and maternal data and these are caused by electrical noise (either EMG or man made) detected on the mothers abdomen and an inadequate heart rate extraction algorithm.

It is possible to remove these errors by passing the raw heart rate data through a post-processing procedure. This is usually only necessary for the raw fetal heart rate data since the maternal consists of very few errors. All fHR data files are passed through this post-processing algorithm. On some occasions, when no errors exist, this post processing will not change the raw fetal heart rate data and hence a true beat to beat heart rate file is available.

Wrong detection or missed ECG complexes will generate 'spikes' up or down on the heart rate trace, creating a variability in the heart rate trace that does not actually exist. In the case of a genuine arrhythmia (i.e. large single beat variations in heart rate values caused by cardiac conduction disorders) these beats can be incorrectly suppressed by the proposed post-processing technique. In cases with patients having arrhythmia then the raw heart rate data file should be used—however, this occurs very infrequently (less than 0.2% of patients).

Also, it is found that on average about 10% of occasions the fetal ECG is coincident with the maternal ECG. If the mECG removal is carried out by blanking (instead of subtracting the mECG template) then this will create an artificial fetal bradycardia. The running of the post-processing is therefore essential to remove artificial fetal bardycardia.

Another problem is that the above fetal heart rate extraction algorithm produces an output whether the fECG signal is present or not. It is very important that in the case of no fECG signal then no fHR trace must be displayed to the clinicians.

Hence, it is necessary for all these reasons, that the beat to beat trace must be post-processed before being plotted for clinical analysis.

Finally it is usual to present fHR data using the standard Cardiotocograph (CTG) output format (obtained from Doppler ultrasound machines) so that easy comparison can be made between the two methods. The standard Doppler ultrasound machines do not give beat to beat value but present an average value. The post-processing to be presented also has the ability to average the heart rate so as to be compatible with the CTG traces.

The post-processing scheme is the same for both the maternal and fetal heart beat interval values (both referred to as "RR intervals") and is made up of two passes.

The first stage selects from the RR intervals those which can be considered as 'good' (i.e "sure") values. It is not important to select all the 'good' values, but it is very important at this stage not to select a wrong RR interval. The condition of selection must then be very strict since the correction of subsequent data is based on this 'good' data.

The second stage will look either side of these selected 'good' values and decide if the beat to beat variability (as entered by the user) is correct. If it is not, the software will attempt to correct the data. This second pass can correct from one to four consecutive errors.

First Stage

The first stage involves analyzing the RR values and selecting those having a small standard deviation. A running window of 4 consecutive RR's are taken and the standard deviation of the data must not exceed typically 7 ms (but set by the user), else the data will be rejected.

On average, it is found that typically 5% of the raw fetal heart rate data are selected at this first stage. The selected 'good' RR intervals are the basis of the eventual subsequent corrections and cannot therefore be corrected themselves. The correction scheme applies to the correction of both the fetal and maternal RR interval data.

For the fetal heart rate data there is an extra condition. Here, in order to be selected by the first pass, the heart beats detected must not have their "coincidence flag" set. This is to avoid a bad mECG subtraction creating an artificial fHR.

Second Stage

The RR intervals not selected above are the values that can be corrected in this second pass. A RR interval is not corrected if it differs by less than 10 percent from a running average (on the three last 'good' RR) or on a neighbor RR with a small standard deviation (set by the user). If the RR interval is not in that range the algorithm looks at the following RR values and will perform a correction if a maximum of four consecutive errors have occurred.

There are two possible error sources:
1. A heart beat has been missed.
2. There was a detection error, i.e. the detected signal does not correspond to a heart beat.

By calling T a detected true heart beat, E a detection error and M a missed heart beat, the possible sequences that the second part of the post-processing can correct are:

| | |
|---|---|
| One error: | TET, TMT. |
| Two consecutive errors: | TEET, TEMT, TMET, TMMT. |
| Three consecutive errors: | TEEET, TEEMT, TEMET, TMEET, TEMMT, TMEMT, TMMET, TMMMT. |
| Four consecutive errors: | TEEEET, TEEEMT, TEEMET, TEMEET, TMEEET, TEEMMT, TEMEMT, TMEEMT, TEMMET, TMEMET, TMMEET, TEMMMT, TMEMMT, TMMEMT, TMMMET, TMMMMT. |

Consider the example where only one error occurs. If this is a detection error, then the wrong RR is simply removed. If there was a missed RR, the corrected RR interval will correspond to a heart beat placed in the middle of the interval between the previous and next 'good' heart beat.

If there is ambiguity with two possible faults, priority is given to the fault pattern which corresponds to the smallest number of errors. In general if a fECG signal is present, most of the faults will be made of just one error.

This correction scheme allows recovery of the discarded fetal heart beats when using the extraction with mECG blanking.

Finally, if no 'good' data (from the first pass) is found within a one minute interval, the fECG signal will be considered not present, no correction will be done and no output will be plotted within that interval.

The post processing can also operate to average the beat-to-beat heart rate data. The interest of doing so is that it allows a better visual comparison with the standard Doppler CTG traces, which usually contain some kind of averaging. Typically a two-second averaging is used.

Figure 12A:
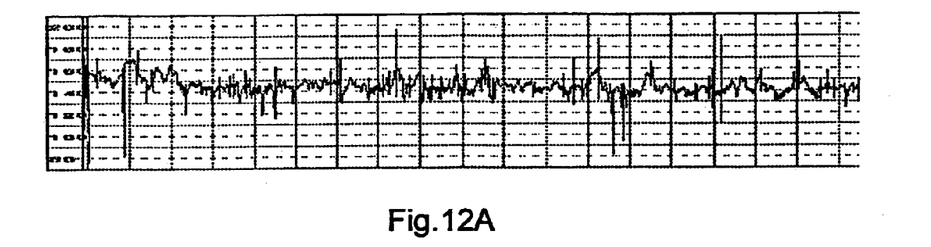
Figure 12B:
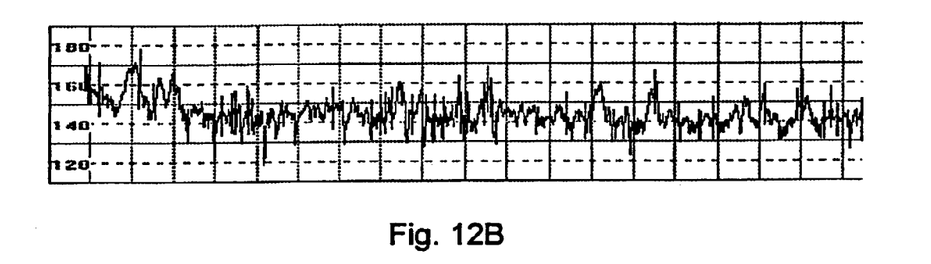
Figure 12C:
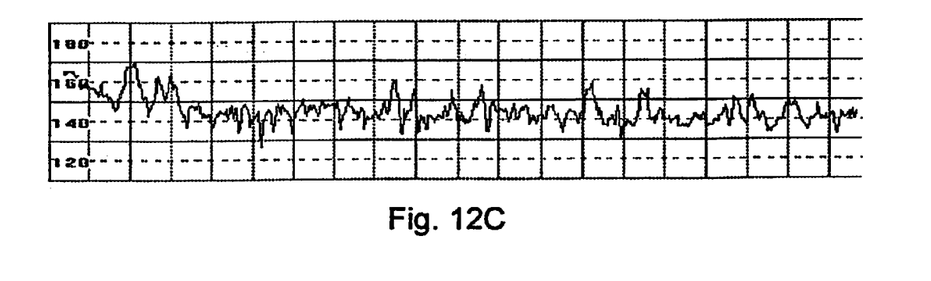
Figure 12D:
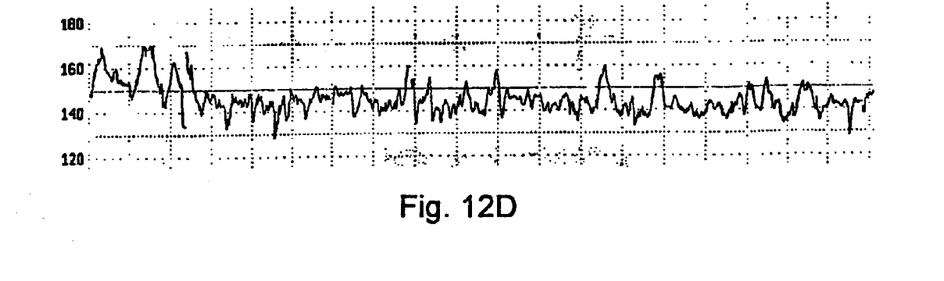

FIGS. 12A to 12D show the fHR versus time of an example of the post-processing of raw abdominal fHR data. FIG. 12A shows the raw fHR data, FIG. 12B shows the post-processed fHR data and FIG. 12C shows the post-processed data after implementing a 2 second average. As a comparison FIG. 12D shows a simultaneous Doppler ultrasound CTG trace which shows excellent correlation illustrating that the post-processing has correctly processed the raw abdominal fHR data.

The invention claimed is:

1. An apparatus for detecting the heart rate of a fetus, the apparatus comprising:
   at least two detectors to detect heart beats of the fetus, each detector including at least two electrodes, adapted to be placed on an abdomen of a mother of the fetus, configured to detect ECG signals; and
   a processor, coupled to the detectors, adapted to determine a heart rate of the fetus by only processing the ECG signals received from the at least two electrodes of each detector, the processor including
      means for detecting heart beats of the mother by determining when the ECG signals reach a maximum, and means for determining a heart rate of the mother by determining a time interval between adjacent heart beats, so as to determine the heart rate of the mother using only the processed ECG signals, wherein the processor generates virtual ECG signals as a weighted sum of the ECG signals detected by the detectors, the virtual ECG signals representing the ECG signals that would have been obtained from a virtual detector positioned at a virtual location on the abdomen of the mother.

2. An apparatus for detecting the heart rate of a fetus, the apparatus comprising:

a detector to detect heart beats of the fetus, the detector including at least two electrodes, adapted to be placed on an abdomen of a mother of the fetus, configured to detect ECG signals; and a processor, coupled to the detector, adapted to determine a heart rate of the fetus by only processing the ECG signals received from the at least two electrodes, the processor including means for detecting heart beats of the mother by determining when the ECG signals reach a maximum, and means for determining a heart rate of the mother by determining a time interval between adjacent heart beats, so as to determine the heart rate of the mother using only the processed ECG signals, wherein the processor is adapted to determine the standard deviation of each time interval between the heart beats detected, and select the time intervals having a standard deviation lower than a predetermined value, so as to determine the heart rate in accordance with the time interval between adjacent heart beats.

3. An apparatus according to claim 2, wherein the predetermined value is approximately 7 ms for four consecutive time intervals.

4. An apparatus according to claim 2, wherein the processor is adapted to designate time intervals not selected to be erroneous time intervals; and modify the erroneous time intervals in accordance with the selected time intervals.

5. An apparatus according to claim 4, wherein to modify the time intervals comprises:

comparing the erroneous time interval to the selected time intervals;

determining the number of errors within the erroneous time interval;

identifying possible fetal heart beats within the erroneous time intervals; and determining the true fetal heart beat from the possible fetal heart beats, based upon the signature of the fetal heart beat.

6. An apparatus according to claim 5, the processor being further adapted to average the time intervals and the corrected time intervals to determine a heart rate.

\* \* \* \* \*